United States Patent
Bosio et al.

(10) Patent No.: US 10,273,295 B2
(45) Date of Patent: Apr. 30, 2019

(54) CHIMERIC ANTIGEN RECEPTOR SPECIFIC FOR SSEA4 ANTIGEN

(71) Applicant: Miltenyi Biotec GmbH, Bergisch Gladbach (DE)

(72) Inventors: Andreas Bosio, Cologne (DE); Olaf Hardt, Cologne (DE); Andrea Aloia, Zurich (CH)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 39 days.

(21) Appl. No.: 15/504,933

(22) PCT Filed: Aug. 12, 2015

(86) PCT No.: PCT/EP2015/068515
§ 371 (c)(1),
(2) Date: Feb. 17, 2017

(87) PCT Pub. No.: WO2016/026742
PCT Pub. Date: Feb. 25, 2016

(65) Prior Publication Data
US 2017/0283489 A1  Oct. 5, 2017

Related U.S. Application Data

(60) Provisional application No. 62/038,873, filed on Aug. 19, 2014.

(51) Int. Cl.
| | | |
|---|---|---|
| C07K 16/30 | (2006.01) | |
| A61K 35/17 | (2015.01) | |
| C07K 16/18 | (2006.01) | |
| A61K 39/00 | (2006.01) | |
| A61K 35/12 | (2015.01) | |
| C07K 14/725 | (2006.01) | |
| A61K 39/395 | (2006.01) | |
| A61K 45/06 | (2006.01) | |
| C07K 14/705 | (2006.01) | |
| C12N 5/0783 | (2010.01) | |

(52) U.S. Cl.
CPC .............. *C07K 16/18* (2013.01); *A61K 35/12* (2013.01); *A61K 35/17* (2013.01); *A61K 39/0011* (2013.01); *A61K 39/3955* (2013.01); *A61K 45/06* (2013.01); *C07K 14/705* (2013.01); *C07K 14/7051* (2013.01); *C07K 14/70517* (2013.01); *C07K 14/70521* (2013.01); *C07K 14/70578* (2013.01); *C07K 16/30* (2013.01); *C12N 5/0636* (2013.01); *A61K 2035/124* (2013.01); *A61K 2039/5156* (2013.01); *A61K 2039/5158* (2013.01); *C07K 2317/24* (2013.01); *C07K 2317/53* (2013.01); *C07K 2317/56* (2013.01); *C07K 2317/622* (2013.01); *C07K 2317/73* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 2014/0099340 A1 | 4/2014 | June et al. | |
| 2016/0280794 A1* | 9/2016 | Wong | C07K 16/30 |
| 2016/0289340 A1* | 10/2016 | Wong | C07K 16/44 |
| 2017/0335281 A1* | 11/2017 | Loew | C12N 5/0638 |

FOREIGN PATENT DOCUMENTS

| | | |
|---|---|---|
| EP | 292738 | 10/2015 |
| EP | 2711418 A1 | 8/2017 |
| WO | 2009/072003 | 6/2009 |
| WO | 2013/040557 | 3/2013 |
| WO | 2014/031687 | 2/2014 |
| WO | 2015/142675 | 9/2015 |
| WO | 2016/026742 | 2/2016 |

OTHER PUBLICATIONS

Church et al., Lineage-Specific Biology Revealed by a Finished Genome Assembly of the Mouse. PLoS Bio, 2009,I 7(5): e1000112. pp. 1-16 (Year: 2009).*
Huang et al, "Carbohydrate-based vaccines with a glycolipid adjuvant for breast cancer", Proceedings of the National Academy of Sciences, vol. 110, No. 7, Jan. 25, 2013.
Hung et al, "Investigation of SSEA-4 Binding Protein in Breast Cancer Cells", Journal of the American Chemical Society, vol. 135, No. 16, Apr. 24, 2013.
International Search Report issued in PCT/EP2015/068515, dated Oct. 15, 2015.
Lou et al, "Stage-specific embryonic antigen-4 as a potential therapeutic target in glioblastoma multiforme and other cancers", Proceedings of the National Academy of Sciences, vol. 111, No. 7, Feb. 3, 2014.
Hudis and Gianni, "Triple-negative breast cancer: an unmet medical need," Oncologist 16(suppl. 1): 1-11, 2011.
Gang et al., "SSEA-4 identifies mesenchymal stem cells from bone marrow," Blood 109(4): 1743-51, Feb. 2007.

(Continued)

*Primary Examiner* — Christopher M Babic
*Assistant Examiner* — Arthur S Leonard
(74) *Attorney, Agent, or Firm* — Fish & Richardson P.C.

(57) ABSTRACT

The present invention provides chimeric antigen receptors (CARs) comprising an antigen binding domain specific for SSEA4, a population of engineered cells expressing said CARs, and a pharmaceutical composition comprising said genetically modified cells expressing said CARs. The pharmaceutical composition may be for use of the treatment of cancer in a subject suffering from cancer, wherein at least a subpopulation of the cancerous cells of said cancer expresses SSEA4.

13 Claims, 6 Drawing Sheets
Specification includes a Sequence Listing.

(56) References Cited

OTHER PUBLICATIONS

Kannagi et al., "Stage-specific embryonic antigens (SSEA-3 and -4) are epitopes of a unique globo-series ganglioside isolated from human teratocarcinoma cells" EMBO J. 2(12): 2355-66, 1983.

Saito et al., "Human α2,3-sialyltransferase (ST3Gal II) is a stage-specific embryonic antigen-4 synthase," J. Biol. Chem. 278(29): 26474-9, Jul. 2003.

Truong et al., "SSEA4 is a potential negative marker for the enrichment of human corneal epithelial stem/progenitor cells," Invest. Ophthalmol. Vis. Sci. 52(9): 6315-6320, Aug. 2011.

* cited by examiner

```
MDFQVQIFSFLLISASVIMSRQVQLKESGPGLVAPSQSLSITCTVSGFSLSSQGVYWVRQPPGKGLEWLGAIWAGGSTNYNSALMSRLSISKDNSKSQVFLKMNSLQT
>>....Lkappa_Signal>>.....................................................................................>
>>..._Peptide             >>.............SSEA-4_VH.................................................

DDTAMYYCARVDGYRGYNMDYWGQGTSVTVSSGGGGSGGGGSGGGGSENVLTQSPAIMSASPGEKVTMTCSASSSVSYMHWYQQKSTSPKLWIYDTSKLASGVPGRF
>........SSEA-4_VH........................>>..............................................................>
                                           >>.GS-Linker.>>.............SSEA-4_VL...........................

SGSGSGNSYSLTISSMEAEDVATYYCFQGSGYPLTFGAGTKLELKAAALPAEPKSPDKTHTCPPCPAPPVAGPSVFLFPPKPKDTLMIARTPEVTCVVVDVSHEDPEV
>.........SSEA-4_VL........................>>..............................................................>
                                            >>>>
                                            AAL-Linker
                                                >>.............................IgG_delta_(Hinge).............

KFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEW
>......................................IgG_delta_(Hinge)....................................................>

ESNGQPENNYKTTPPVLDSDGSFFLYSKLTVDKSRWQQGNVFSCSSVMHEALHNHYTQKSLSLSPGKKIYIWAPLAGTCGVLLLSLVITLYCKRGRKKLLYIFKQPFM
>.........................IgG_delta_(Hinge)..............>>.................CD8alpha........>>
                                                                                              >>..4-1BB ......>

RPVQTTQEEDGCSCRFPEEEEGGCELLRVKFSRSADAPAYQQGQNQLYNELNLGRREEYDVLDKRRGRDPEMGGKPRRKNPQEGLYNELQKDKMAEAYSEIGMKGERR
>............4-1BB............................>>............................................................>
                                               >>..........................CD3_zeta.........................

RGKGHDGLYQGLSTATKDTYDALHMQALPPR-
>.............CD3_zeta............>>

FIG 2A
```

MDFQVQIFSFLLISASVIMSRENVLTQSPAIMSASPGEKVTMTCSASSSVSYMHWYQQKSTSPKLWIYDTSKLASGVPGRFSGSGSGNSYSLTISSMEAEDVATYYC
>>....Lkappa_Signal>>
_Peptide                >>.................................................SSEA-4_VL.................................^

FQGSGYPLTFGAGTKLELKGGGGSGGGGSGGGGSQVQLKESGPGLVAPSQSLSITCTVSGFSLSSQGVYWVRQPPGKGLEWLGAIWAGGSTNYNSALMSRLSISKDNS
^....SSEA-4_VL.....>>     >>.GS-Linker.>>
                                        >>..................................................SSEA-4_VH.................^

KSQVFLKMNSLQTDDTAMYYCARVDGYRGYNMDYWGQGTSVTVSSAAALPAEPKSPDKTHTCPPCPAPPVAGPSVFLFPPKPKDTLMIARTPEVTCVVVDVSHEDPEV
^.................SSEA-4_VH.................>>
                                              >>>>
                                              AAAL-Linker
                                                  >>..........................................IgG_delta_(Hinge).........^

KFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEW
^.................................................IgG_delta_(Hinge).........................................^

ESNGQPENNYKTTPPVLDSDGSFFLYSKLTVDKSRWQQGNVFSCSSVMHEALHNHYTQKSLSLSPGKKIYIWAPLAGTCGVLLLSLVITLYCKRGRKKLLYIFKQPFM
^.........IgG_delta_(Hinge)...........>>
                                        >>......CD8alpha........>>
                                                                   >>..4-1BB.....^

RPVQTTQEEDGCSCRFPEEEEGGCELLRVKFSRSADAPAYQQGQNQLYNELNLGRREEYDVLDKRRGRDPEMGGKPRRKNPQEGLYNELQKDKMAEAYSEIGMKGERR
^....4-1BB....................>>
                                 >>......................................CD3_zeta................^

RGKGHDGLYQGLSTATKDTYDALHMQALPPR-
^..........CD3_zeta.............>>

FIG 2B

A
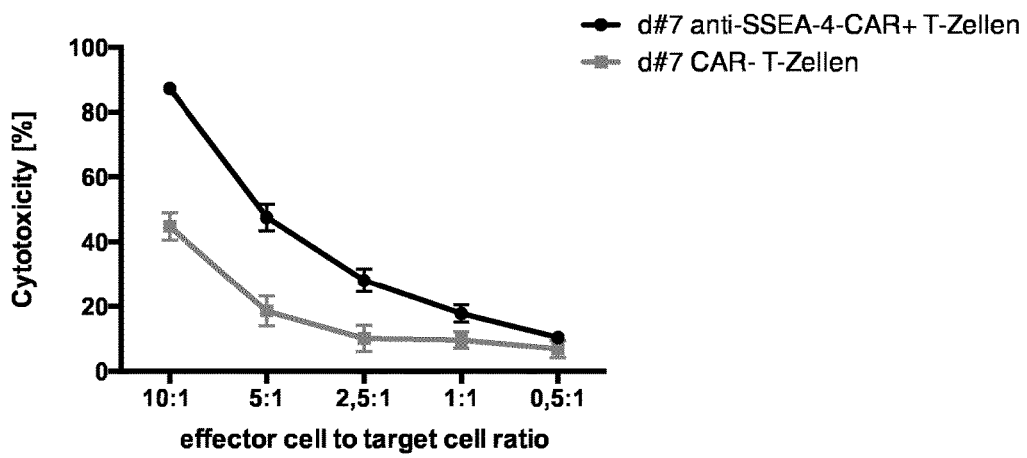
B
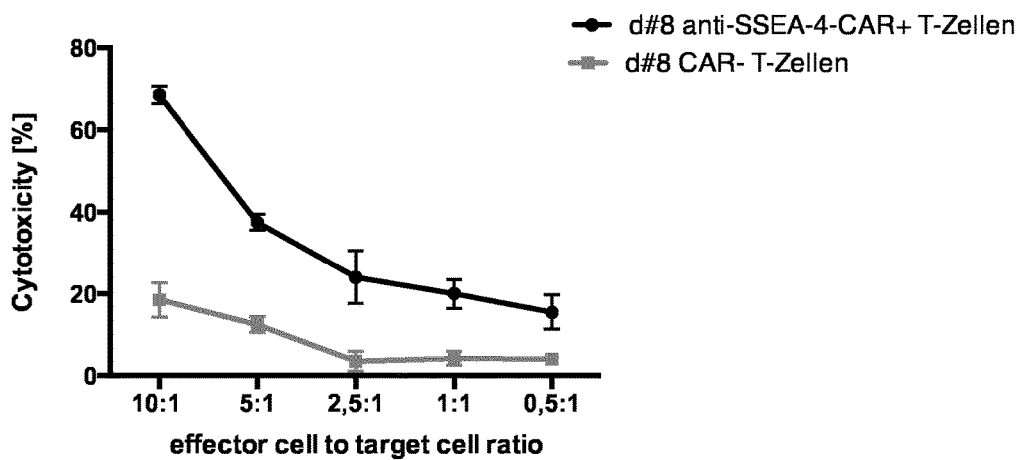
FIG 5

CHIMERIC ANTIGEN RECEPTOR SPECIFIC FOR SSEA4 ANTIGEN

CROSS-REFERENCE TO RELATED APPLICATIONS

This application is a 371 U.S. National Stage Application of PCT Application No. PCT/EP2015/068515, filed on Aug. 12, 2015, which claims the benefit of priority under 35 U.S.C. § 119(e) to U.S. Application No. 62/038,873, filed on Aug. 19, 2014, the entire contents of which are incorporated herein by reference.

FIELD OF INVENTION

The present invention relates to the field of treatment of cancer, in particular to the treatment of cancer by using the antigen SSEA4 as a target.

BACKGROUND

Cancer is a broad group of diseases involving unregulated cell growth. In cancer, cells divide and grow uncontrollably, forming malignant tumors, and invading nearby parts of the body. The cancer may also spread to more distant parts of the body through the lymphatic system or bloodstream. There are over 200 different known cancers that affect humans. Whereas good treatment options are available for many cancer types, others still represent unmet medical needs. In particular, ovarian cancer, renal cell carcinoma, and triple negative breast cancer (TNBC) are malignancies with limited therapeutic options. TNBC is an aggressive subtype of breast cancer associated with high risk of metastasis and early relapse. Currently the main option for systemic therapy of TNBC patients is chemotherapy with an overall poor efficacy and severe side effects. Initially, the majority of TNBC patients respond to neoadjuvant chemotherapy treatment, but only about 20% reach a pathological complete response (pCR) with good prognosis. Notably, most patients do not reach pCR because tumors either have lower de novo sensitivity to chemotherapy or develop resistance to chemotherapy. In such cases, tumors regress due to chemotherapy, but residual cancer cells persist and initiate tumor recurrence and metastasis within three years after chemotherapy in about 40% of patients.

Sialyl-glycolipid stage-specific embryonic antigen 4 (SSEA4) is a sialyl-glycolipid epitope also known as monosialosyl globopentaosylceramide (MSGb5), initially identified on human teratocarcinoma cells (Kannagi R et al., EMBO J. 1983; 2(12):2355-61; Saito S et al., J Biol Chem. 2003 Jul. 18; 278(29):26474-9). SSEA4 is found on undifferentiated human embryonic stem (ES) cells, induced pluripotent (iPS) cells, embryonal carcinoma (EC) cells, and embryonic germ (EG) cells and a variety of somatic stem cells, such as dental pulp stem cells, umbilical cord blood-derived very small embryonic like stem cells (VSELs) and mesenchymal stromal cells (Gang E J et al., Blood. 2007 Feb. 15; 109(4):1743-51; Truong T T et al., Invest Ophthalmol Vis Sci. 2011 Aug. 11; 52(9):6315-20).

In EP14305477.3 it is disclosed that SSEA4 is a biomarker to mark a subpopulation of chemotherapy resistant cancer cells.

The function of SSEA4 is still unknown.

The chimeric antigen receptor (CAR) provides a promising approach for adoptive cell immunotherapy for cancer. Commonly, CARs comprise a single chain fragment variable (scFv) of an antibody specific for a tumor associated antigen (TAA) coupled via hinge and transmembrane regions to cytoplasmic domains of T-cell signaling molecules. The most common lymphocyte activation moieties include a T-cell costimulatory (e.g. CD28, CD137, OX40, ICOS, and CD27) domain in tandem with a T-cell triggering (e.g. CD3ζ) moiety. The CAR-mediated adoptive immunotherapy allows CAR-grafted cells to directly recognize the TAAs on target tumor cells in a non-HLA-restricted manner.

Although less than 25% of breast cancer patients benefit from chemotherapeutic treatment (CLIFFORD A. HUDIS and LUCA GIANNI, The Oncologist 2011; 16 (suppl 1):1-11), this systemic approach is still used as standard care. Because of the severe side effects, it would be highly beneficial to identify markers which can be used as an option for treatment of cancers such as human breast cancer.

SUMMARY OF THE INVENTION

SSEA4 is a cell surface antigen of cancerous cells and therefore, it can be used for a targeted biological or immunological therapy of cancerous cells expressing SSEA4 including but not limited to ovarian cancer, renal cell carcinoma and TNBC. We now surprisingly found that engineered cells, preferentially engineered T cells expressing a chimeric antigen receptor specific for the antigen SSEA4 are able to kill cells expressing SSEA4 in vitro and in vivo. Therefore, the invention relates to a strategy of adoptive cell transfer of cells transduced to express a chimeric antigen receptor wherein said CAR is targeted to SSEA4 ("SSEA4-CAR"), resulting in the recognition of and binding to the cancerous cells expressing SSEA4. Then the genetically modified cell, i.e. the CAR expressing cell, performs its specific function, for example killing the target cell, secreting cytokines and/or proliferating.

BRIEF DESCRIPTION OF THE DRAWINGS

FIG. 2: Amino acid sequences of (A) full SSEA4-CAR $V_H$-linker-$V_L$ (corresponding to SEQ ID NO:5) and (B) full SSEA4-CAR $V_L$-linker-$V_H$ (corresponding to SEQ ID NO:6)

FIGS. 5A and B: SSEA-4-CAR-dependent killing of SSEA-4-positive tumor cells by transduced T cells

DETAILED DESCRIPTION OF THE INVENTION

Figure 1:
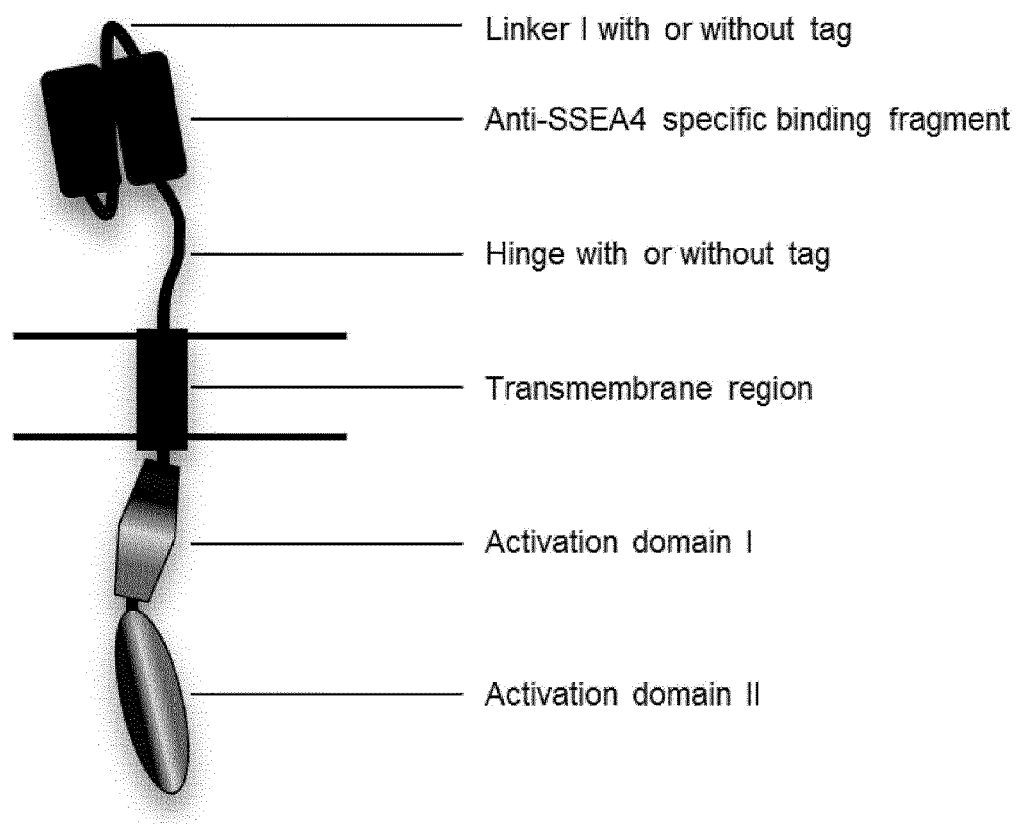
FIG. 1: Structure of a CAR recognizing SSEA4

Surprisingly, we found that SSEA4 expressing cancerous cells which are directly targeted by an engineered immune cell expressing a CAR specific for the antigen SSEA4 are affected in a manner that these cells fail to grow and/or are prompted to die.

In a first aspect the invention provides a chimeric antigen receptor (CAR) comprising an antigen binding domain specific for SSEA4 ("SSEA4-CAR").

The antigen binding domain of said SSEA4-CAR may comprise, for example, full length heavy chain, Fab fragments, single chain Fv (scFv) fragments, divalent single chain antibodies or diabodies, each of which are specific for the target antigen SSEA4.

The antigen binding domain of said CAR may comprise the amino acid sequences of SEQ ID NO:1 and SEQ ID NO:2. The antigen binding domain of said CAR may comprise a scFv comprising the amino acid sequence of SEQ ID NO:3 or SEQ ID NO:4. Said CAR may comprise the amino acid sequences of SEQ ID NO:5 or SEQ ID NO:6.

Said CAR may comprise a transmembrane domain and a intracellular signaling domain, wherein the transmembrane domain comprises e.g. a sequence of the transmembrane domains derived from CD8alpha and/or CD28; and wherein the intracellular signaling domain comprises e.g. a sequence derived from the intracellular signaling domains of one or more of CD28, CD137, OX40 and CD3zeta. Alternatively, the CAR may be composed of further parts such as a linker and/or hinge (see FIG. 1) and/or may be composed as di- or multi-chain CAR as described below.

The SSEA4-CAR may comprise the amino acid sequence of SEQ ID NO:5 or SEQ ID NO:6.

In one aspect of the invention the CAR of the invention is for the treatment of cancer in a subject suffering from cancer, and wherein at least a subpopulation of the cancerous cells of said cancer expresses SSEA4.

Said cancer may be selected from the group consisting of human breast cancer, human renal cell carcinoma (RCC) and human ovarian cancer. Said cancer may be TNBC.

Said subpopulation of cancerous cells expressing SSEA4 may comprise at least 1 cell which expresses SSEA4 out of all cancerous cells in the subject suffering from said cancer. Preferentially said subpopulation of cancerous cells expressing SSEA4 may comprise at least 1%, at least 5%, at least 10%, at least 15%, at least 20%, at least 25%, at least 30%, at least 35%, at least 40%, at least 45% or at least 50% of all cancerous cells of a subject suffering from said cancer.

The treatment of cancer may encompass any method which involves SSEA4 as a target molecule. Such methods may be e.g. treatment with agents which bind to the molecule SSEA4 and affect the viability of the cancerous cell expressing SSEA4, preferentially kill the cancerous cell expressing SSEA4. Examples are oncolytic viruses, BiTEs®, ADCCs and immunotoxins.

An oncolytic virus is a virus that preferentially infects and kills cancer cells. As the infected cancer cells are destroyed by lysis, they release new infectious virus particles to help destroy the remaining tumor. Oncolytic viruses are thought not only to cause direct destruction of the tumor cells, but also to stimulate host anti-tumor immune responses. Specific targeting (e.g. targeting to SSEA4) involves modifying the viral coat proteins to target tumor cells (e.g. with antigen binding domain specific for SSEA4) while reducing entry to non-tumor cells.

Bi-specific T-cell engagers (BiTEs®) are a class of artificial bispecific monoclonal antibodies that are investigated for the use as anti-cancer drugs. They direct a host's immune system, more specifically the T cells' cytotoxic activity, against cancer cells.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to a tumor cell via a tumor specific molecule (e.g. SSEA4). Like other bispecific antibodies, and unlike ordinary monoclonal antibodies, BiTEs® form a link between T cells and tumor cells. This causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells. Antibody-dependent cell-mediated cytotoxicity (ADCC) is a mechanism of attack by the immune system that requires the presence of antibodies bound to the surface of target cells. Antibodies are formed of a binding region (Fab), which binds to the target antigen, e.g. SSEA4, and the Fc region that can be detected by immune cells via Fc receptors on their surface. These Fc receptors are found on the surface of many cells of the immune system, including natural killer cells. When a natural killer cell encounter cells coated with antibodies, the Fc regions interact with their Fc receptors, leading to the release of perforin and granzyme B. These two chemicals lead to the tumor cell initiating programmed cell death (apoptosis). Antibodies known to induce this method of cell killing include Rituximab, Ofatumumab, Trastuzumab, Cetuximab and Alemtuzumab. Third generation antibodies that are currently being developed have altered Fc regions that have higher affinity for a specific type of Fc receptor, FcγRIIIA, which can increase the rate of ADCC dramatically.

An immunotoxin is a human-made protein that consists of a targeting portion (e.g. targeted to SSEA4) linked to a toxin. When the protein binds to that cell, it is taken in through endocytosis, and the toxin kills the cell. These chimeric proteins are usually made of a modified antibody or antibody fragment, attached to a fragment of a toxin. The "targeting portion" is composed of the Fv portion of an antibody that binds specifically to an antigen expressed by a cell, preferably by a specific cell type (e.g. an SSEA4 expressing cell). The toxin is usually a cytotoxic protein derived from a bacterial or plant protein, from which the natural binding domain has been removed so that the Fv directs the toxin to the antigen on the target cell.

In a preferred embodiment of the invention, the SSEA4 expressing cancerous cell is targeted by a engineered cell, preferentially T cell, expressing a chimeric antigen receptor specific for SSEA4 as disclosed herein. This engineered (T) cell may be used in adoptive (T) cell therapy.

In an aspect the invention provides a population of cells comprising genetically modified cells expressing a chimeric antigen receptor specific for the antigen SSEA4 (SSEA4-CAR) as disclosed herein. Preferentially said population of cells comprising genetically modified cells expressing a chimeric antigen receptor specific for the antigen SSEA4 (SSEA4-CAR) is an isolated population of cells.

In one aspect the invention provides a population or an isolated population of engineered cells expressing SSEA4-CAR as disclosed herein for use in immunotherapy. The immunotherapy may be for treatment of cancer in a subject suffering from cancer, wherein at least a subpopulation of the cancerous cells of said cancer express SSEA4.

Said subpopulation of cancerous cells expressing SSEA4 may comprise at least 1 cell which expresses SSEA4 out of all cancerous cells in the subject suffering from said cancer. Preferentially said subpopulation of cancerous cells expressing SSEA4 may comprise at least 1%, at least 5%, at least 10%, at least 15%, at least 20%, at least 25%, at least 30%, at least 35%, at least 40%, at least 45% or at least 50% of all cancerous cells of a subject suffering from said cancer.

In case of need, said population or isolated population of engineered cells are expanded to therapeutically effective amount of cells before use in said immunotherapy. Said cancer may be selected from the group consisting of human breast cancer, human renal cell carcinoma (RCC) and human ovarian cancer. Said cancer may be TNBC. Said cells may be immune cells or immune cell subsets, preferentially T cells or T cell subsets or NK cells or NK cells subsets.

In one aspect the invention provides a method of treating cancer comprising administering to a subject in need thereof an amount of enriched, engineered cells expressing SSEA-CAR as disclosed herein effective to treat said cancer. The treatment of cancer may be in a subject suffering from cancer, wherein at least a subpopulation of the cancerous cells of said cancer express SSEA4.

Said cancer may be selected from the group consisting of human breast cancer, human renal cell carcinoma (RCC) and human ovarian cancer. Said cancer may be TNBC. Said cells may be immune cells or immune cell subsets, preferentially T cells or T cell subsets or NK cells or NK cells subsets.

In one aspect the invention provides a pharmaceutical composition comprising genetically modified cells expressing a CAR specific for the antigen SSEA4 as disclosed herein and a pharmaceutical acceptable carrier.

Said pharmaceutical composition may be used in the treatment of cancer in a subject suffering from cancer. Said cancer may be selected from the group consisting of human breast cancer, human renal cell carcinoma (RCC) and human ovarian cancer. Said cancer may be TNBC. Said cells may be immune cells or immune cell subsets, preferentially T cells or T cell subsets or NK cells or NK cells subsets.

In one aspect the invention provides a pharmaceutical composition comprising genetically modified cells expressing SSEA-CAR as disclosed herein and a pharmaceutical acceptable carrier and a chemotherapeutical agent for combined treatment of said cancer.

In an aspect the invention provides nucleic acids molecules and nucleic acids constructs such as vectors which encode for the SSEA4-CAR of the present invention as disclosed herein.

Adoptive cell transfer uses immune cell-based, preferentially T cell-based cytotoxic responses to attack cancer cells. Immune cells, preferentially T cells that have a natural or genetically engineered reactivity to a patient's cancer are generated in vitro and then transferred back into the cancer patient. The chimeric antigen receptor provides a promising approach for this adoptive cell immunotherapy for cancer. The CAR of the invention can be engineered to comprise an extracellular domain having an antigen binding domain fused to an intracellular signaling domain of the T cell antigen receptor complex zeta chain, e.g. CD3 zeta. Extracellular and intracellular domains may be directly linked via a transmembrane domain or the extracellular domains may be fused to an transmembrane domain and the intracellular domains may be fused to another transmembrane domain. If the extra- and intracellular domains are linked to separate transmembrane domains then the transmembrane domains interact for activation of the CAR (split CAR or multi chain CAR). Engineered immune cells, preferentially T cells of the invention express a CAR of the invention which is able to redirect antigen recognition based on the antigen binding specificity of the CAR. The specificity of the CAR is for the antigen SSEA4 which is found to be expressed on cancerous cells such as human breast cancer, RCC and human ovarian cancer.

In general a CAR may comprise an extracellular domain comprising the antigen binding domain, a transmembrane domain and an intracellular signaling domain. The extracellular domain may be linked to the transmembrane domain by a linker. The extracellular domain may also comprise a signal peptide.

A "signal peptide" refers to a peptide sequence that directs the transport and localization of the protein within a cell, e.g. to a certain cell organelle (such as the endoplasmic reticulum) and/or the cell surface.

An "antigen binding domain" refers to the region of the CAR that specifically binds to an antigen (and thereby is able to target a cell containing an antigen). The CARs of the invention may comprise one or more antigen binding domains. Generally, the targeting regions on the CAR are extracellular. The antigen binding domain may comprise an antibody or a fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors can be used as an antigen binding domain. Often the antigen binding domain is a scFv. Normally, in a scFv the variable portions of an immunoglobulin heavy chain and light chain are fused by a flexible linker to form a scFv. Such a linker may be for example the "$(G_4/S_1)_3$-linker".

In some instances, it is beneficial for the antigen binding domain to be derived from the same species in which the CAR will be used in. For example, if it is planned to use it therapeutically in humans, it may be beneficial for the antigen binding domain of the CAR to comprise a human or humanized antibody or fragment thereof. Human or humanized antibodies or fragments thereof can be made by a variety of methods well known in the art. "Spacer" or "hinge" as used herein refers to the hydrophilic region which is between the antigen binding domain and the transmembrane domain. The CARs of the invention may comprise an extracellular spacer domain but is it also possible to pass such a spacer. The spacer may include Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge.

The transmembrane domain of the CAR can be derived from any desired natural or synthetic source for such domain. If the source is natural the domain may be derived from any membrane-bound or transmembrane protein. The transmembrane domain may be derived for example from CD8alpha or CD28.

The cytoplasmic domain or the intracellular signaling domain of the CAR of the invention is responsible for activation of at least one of the normal effector functions of the immune cell in which the CAR is expressed. "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR of the invention to perform a specialized function. The intracellular signaling domain may include any complete or truncated part of the intracellular signaling domain of a given protein sufficient to transduce the effector function signal.

Prominent examples of intracellular signaling domains for use in the CARs include the cytoplasmic sequences of the T cell receptor (TCR) and co-receptors that act in concert to initiate signal transduction following antigen receptor engagement.

Generally, T cell activation can be mediated by two distinct classes of cytoplasmic signaling sequence, firstly those that initiate antigen-dependent primary activation through the TCR (primary cytoplasmic signaling sequences) and secondly those that act in an antigen-independent manner to provide a secondary or co-stimulatory signal (secondary cytoplasmic signaling sequences).

Primary cytoplasmic signaling sequences that act in a stimulatory manner may contain ITAMs (immunoreceptor tyrosine-based activation motifs signaling motifs).

Examples of ITAM containing primary cytoplasmic signaling sequences often used in CARs are that are those derived from TCR zeta, FcR gamma, FcR beta, CD3 gamma, CD3 delta, CD3 epsilon, CD5, CD22, CD79a, CD79b, and CD66d. Most prominent is sequence derived from CD3 zeta.

The cytoplasmic domain of the CAR can be designed to comprise the CD3-zeta signaling domain by itself or combined with any other desired cytoplasmic domain(s). The cytoplasmic domain of the CAR can comprise a CD3 zeta chain portion and a costimulatory signaling region. The costimulatory signaling region refers to a part of the CAR comprising the intracellular domain of a costimulatory molecule. A costimulatory molecule is a cell surface molecule other than an antigen receptor or their ligands that is required for an efficient response of lymphocytes to an antigen. Examples for costimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3-zeta and the signaling domain of CD28. In another example the cytoplasmic domain may comprise the signaling domain of CD3-zeta and the signaling domain of CD27. In an further example, the cytoplasmic domain may comprise the signaling domain of CD3-zeta, the signaling domain of CD28, and the signaling domain of CD27.

The CAR of the invention may be designed to comprise any portion or part of the above-mentioned domains as described herein. The specificity of the CAR of the invention mediated by the antigen binding domain is for the antigen SSEA4, all other domains necessary to construct a functional CAR may be chosen from the options mentioned above or which are well known to the person skilled in the art. Exemplary the CAR of the invention may have the amino acid sequence of SEQ ID No:5 or SEQ ID NO:6.

Figure 3:
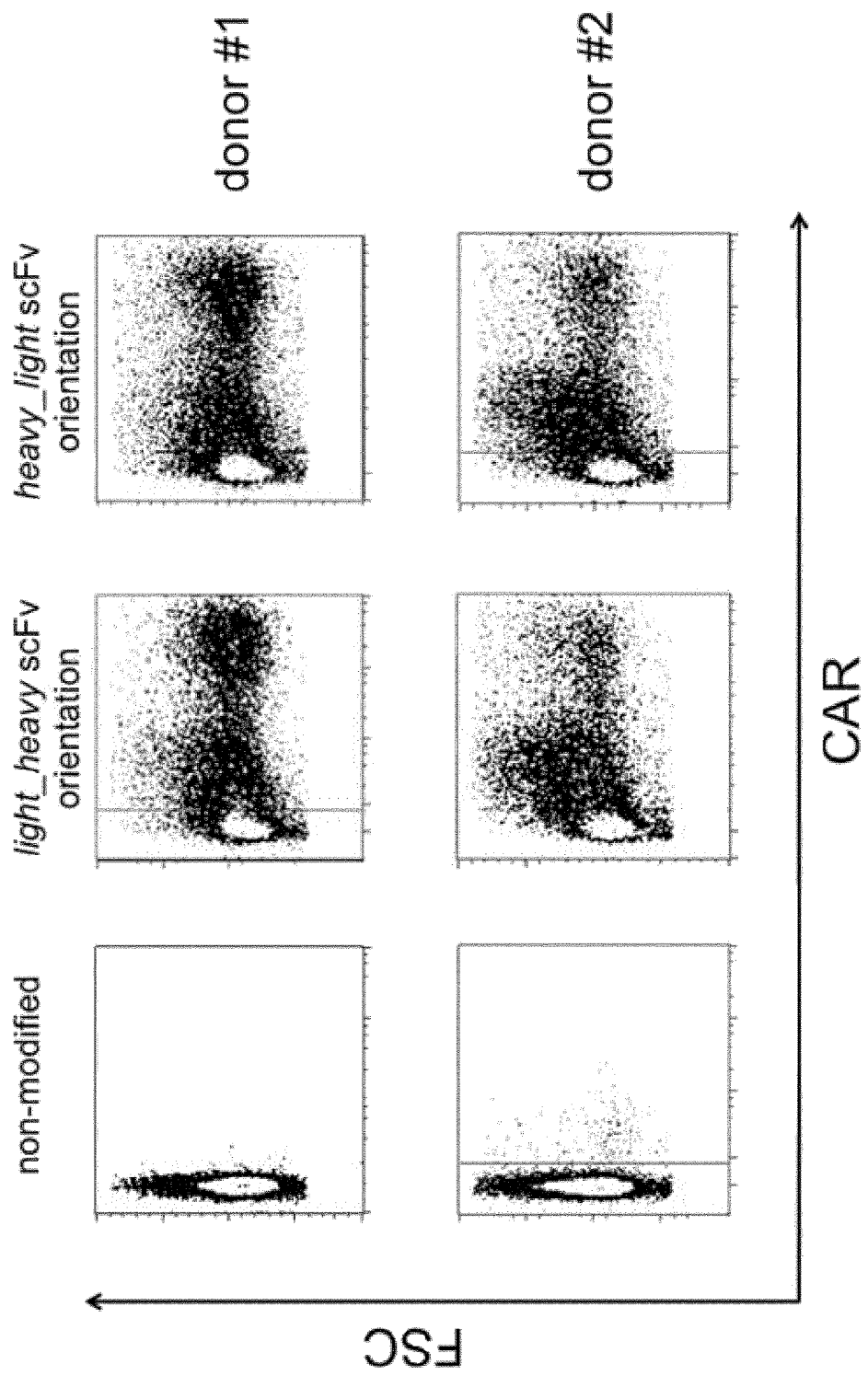
FIG. 3: Expression of the chimeric antigen receptor constructs "heavy_light scFv orientation" (SEQ ID NO:5) and "light_heavy scFv orientation" (SEQ ID NO:6) on the surface of peripheral blood T cells FIGS. 4A, B and C: SSEA-4-CAR-dependent T cell activation following stimulation with SSEA-4-positive tumor cells resulting in secretion of the pro-inflammatory cytokines IFNγ, IL-2, and TNFα

FIG. 3 shows the expression of the chimeric antigen receptor constructs "heavy_light scFv orientation" (SEQ ID NO:5) and "light_heavy scFv orientation" (SEQ ID NO:6) on the surface of peripheral blood T cells including non-modified T lymphocytes. Naive Pan T cells were isolated from peripheral blood mononuclear cells (PBMCs) and cultured in the presence of stimulating matrix (MACS® GMP TransAct CD3/CD28 Kit; Miltenyi Biotec GmbH) as well as IL-2. For permanent receptor expression the lymphocytes were transduced lentivirally with a multiplicity of infection (MOI) of 2. Surface expression was determined flow cytometrically with antibodies directed against the IgG spacer domain.

Figure 4:
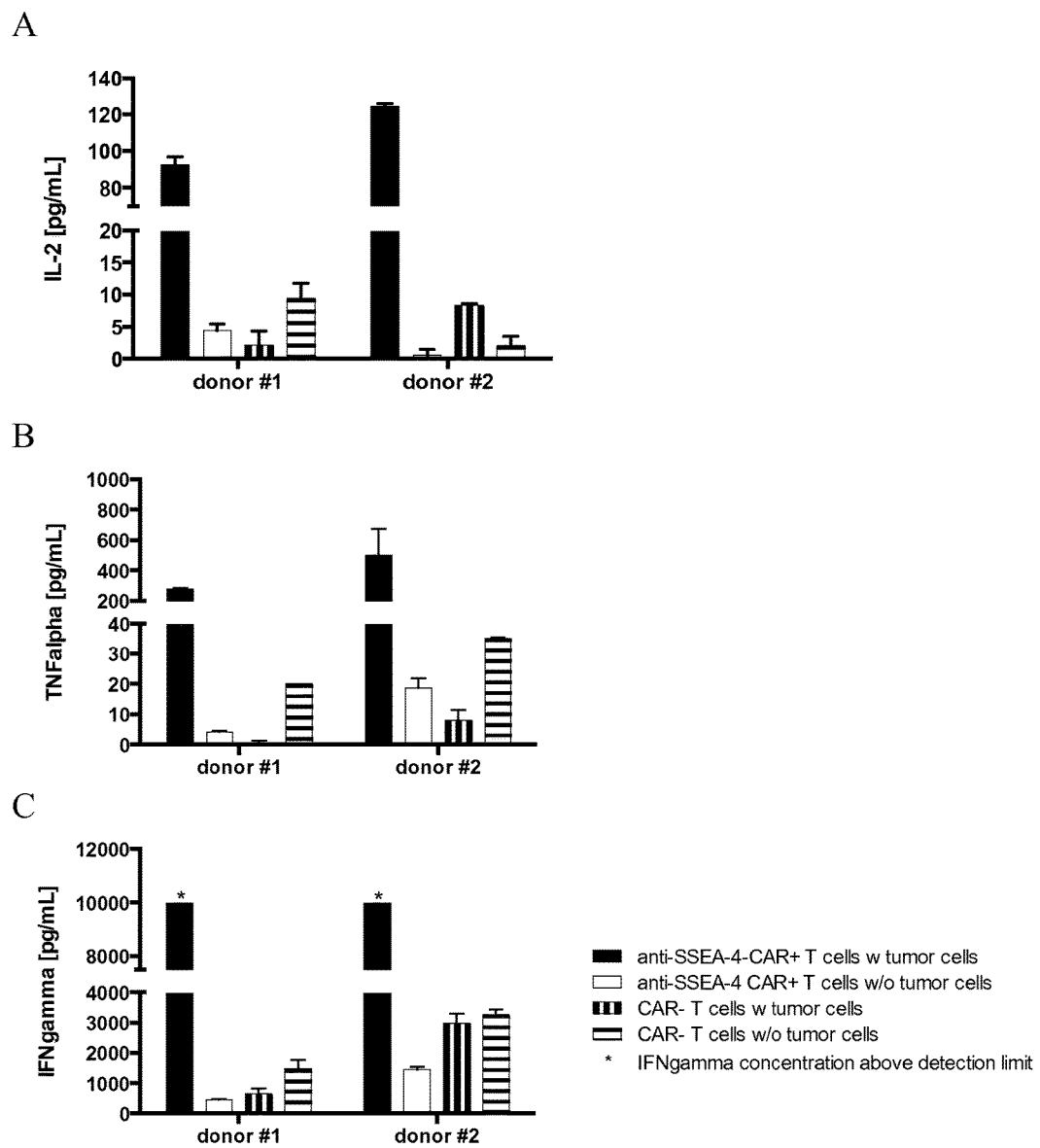

FIG. 4 illustrates CAR-induced secretion of the pro-inflammatory cytokines IL-2 (FIG. 4A), TNFalpha (FIG. 4B), and IFNgamma (FIG. 4C), following stimulation with SSEA-4-positive tumor cells (NTERA2). The experimental results for the light_heavy scFv- and the CH2CH3 spacer domain-bearing receptor construct are shown. $1*10^5$ CAR+ T cells were cocultured with tumor cells at a 1:2 ratio for 24 hours and subsequently the cytokine levels of IL-2, TNFalpha, and IFNgamma were determined using the MACSPlex technique (Miltenyi Biotec GmbH; MACSPlex Assays are designed for determining concentrations of soluble analytes in a single sample. The analysis is based on MACSPlex (MPx) Capture Beads, which display defined fluorescence properties and can be identified using standard flow cytometry techniques. MPx Capture Beads within the MACSPlex Cytokine 12 Kit, human and MACSPlex Cytokine 10 Kit, mouse contain a cocktail of various fluorescently labeled bead populations, each coated with a specific antibody reacting with one of the respective cytokines within the sample.). In parallel, CAR+ T cells were cultured in the absence of antigen stimulus in order to determine the background activity of the chimeric receptors. Control cultures of non-modified T cells with and without tumor cells, respectively, served to assess the specificity of CAR-mediated lymphocyte response. The experiment was performed with two donors and in duplicates and means as well as standard deviations were determined. The ordinate axis represents the concentration of the respective cytokine in pg/mL as determined in the coculture supernatants. After antigen contact, the transgenic T cells of both donors exhibit an at least 10-fold increased secretion in IL-2 (FIG. 4A), TNFalpha (FIG. 4B), and IFNgamma (FIG. 4C) whereas cocultures with non-modified T cells show only negligible amount of cytokine production. Also, in test samples, in which anti-SSEA-4-CAR T cells were cultured without tumor cells, the cytokine production is within "background noise". These results thus verify the functionality of the developed chimeric receptors that activate T cells in an antigen-dependent and CAR-specific manner.

FIG. 5 shows the cytotoxicity assay results for the evaluation of CAR-induced cytolytic activity of modified CD8+ T cells following antigen stimulation. The experimental results for the light_heavy scFv- and the CH2CH3 spacer domain-bearing receptor construct are shown. Effector cells (CD8+ CAR+ T cells) were plated with $1*10^4$ fluorescently labeled SSEA-4-positive tumor cells (NTERA2) at ratios 10:1, 5:1, 2.5:1, 1:1, and 0.5:1. Following 24 hours of coculture, the amount of viable tumor cells was determined by flow cytometry and the cytotoxicity efficiency for each ratio was assessed. For specificity comparison, cocultures with non-modified T cells were used. The experiment was performed with two donors (FIG. 5A: donor #7; FIG. 5B: donor #8) and in quadruplicates and means as well as standard deviations were determined.

Data are shown as the percentage of cytotoxicity compared with NTERA2 target cells incubated in the absence of T cells (0%). For both donor #7 (FIG. 5A) and donor #8 (FIG. 5B) a selective tumor cell killing by CAR+ T cells is observable indicating that CAR activation not only promotes cytokine secretion, but also cytotoxic activity.

Embodiments

The present invention also encompasses nucleic acids (DNA or RNA) constructs comprising sequences encoding for amino acids sequences of a CAR specific for SSEA4.

In one embodiment of the invention a DNA construct (vector, plasmid) is generated encoding for a CAR specific for SSEA4. A nucleic acid sequence encoding for an antigen binding domain specific for SSEA4 is fused at least to a nucleic acid sequence encoding a transmembrane domain and subsequent a nucleic acid sequence encoding a intracellular domain. The construction of such expression vectors can be performed by recombinant methods well known in the art. Alternatively, the nucleic acid sequences can be produced synthetically.

In one embodiment of the invention a cell expressing the CAR of the invention is generated. The DNA construct encoding the CAR of the invention can be transfected or transduced into a host cell by methods well known in the art (e.g. viral-based systems, physical methods, biological methods, chemical methods). Regardless the methods used to integrate, preferentially stably integrate, the nucleic acid encoding the CAR of the invention, in the host cell, as a result the host cell expresses a CAR which is specific for SSEA4.

In one embodiment of the invention the CAR specific for the antigen SSEA4 is expressed in immune cells or immune cell subsets.

In one embodiment of the invention the CAR specific for the antigen SSEA4 is expressed in T cells or T cell subsets.

In one embodiment of the invention the CAR specific for the antigen SSEA4 is expressed in NK cells or NK cell subsets.

In one embodiment of the invention an engineered cell expressing a CAR specific for SSEA4 (the "SSEA4-CAR") is isolated (enriched or separated) after the transfection/transduction process for generating such an engineered SSEA4-CAR cell from non-transfected/transduced cells by methods well known in the art, e.g. fluorescent based separating technologies such as FACS® or magnetic cell separation methods such as MACS®.

In an embodiment of the invention a source of immune cells, preferentially T cells is obtained from a subject. Immune cells, preferentially T cells can be obtained from a variety of sources such as peripheral blood mononuclear cells (PMBCs), bone marrow, lymph node tissue, cord blood or thymus tissue. For enrichment of these cells methods well known in the art can be used such as centrifugation through a Ficoll™ or PERCOLL™ gradient or positive/negative selection techniques such as fluorescent sorting (e.g. FCAS-sort) or magnetic sorting (e.g. MACS®).

In one embodiment T cells of a blood sample of a subject are magnetically labelled, for example with a magnetic bead coupled to antibodies specific for CD4 and for CD8, respectively, washed, magnetically enriched and collected. Then these T cells may be engineered to express the SSEA4-CAR on their cell surface.

In one embodiment of the invention the isolated/enriched engineered T cells expressing SSEA4-CAR prior or after genetic modification can be activated and expanded to increase amount of engineered T cells generally using methods well known in the art, for example polyclonal stimulation with anti-CD3/anti-CD28 beads or anti-CD3/anti-CD28 nanomatrices (EP2711418A1). Preferentially, said amount of engineered T cells is increased to a therapeutic effective amount.

In one embodiment of the invention a cell expressing the CAR of the invention is generated. The RNA encoding the CAR of the invention can be transfected or transduced into a host cell by methods well known in the art (e.g. viral-based systems, physical methods, biological methods, chemical methods). In general, such an "RNA-engineered cell" is disclosed in detail in WO2013/040557. Regardless the methods used to integrate the RNA encoding the CAR of the invention, in the host cell, as a result the host cell expresses a CAR which is specific for SSEA4. Using "RNA-engineered cells" lead to the fact that the CAR is expressed for a limited time in the cell (transient expression).

In one embodiment of the invention the genetically modified cells expressing SSEA4-CAR, preferentially T cells, are generated automatically in a closed cell culture system. A process for generation of genetically modified cells, preferentially T cells, T cell subsets or T cell progenitors comprises the steps:

a) providing a cell sample
b) preparation of the cell sample by centrifugation
c) magnetic separation of the cell, preferentially T cells, T cell subsets or T cell progenitors
d) activation of the enriched cells, preferentially T cells, T cell subsets or T cell progenitors using modulatory agents
e) genetically modifying the cells, preferentially T cells, T cell subsets or T cell progenitors to express SSEA4-CAR
f) expansion of the genetically modified T cells, T cell subsets or T cell progenitors in a cultivation chamber
g) washing of the cultured cells, preferentially T cells, T cell subsets or T cell progenitors.

All these steps may be performed in a closed and sterile system.

The process is especially suited for preparing gene modified cells, preferentially T cells, T cell subsets or T cell progenitors wherein the enriched cells, preferentially T cells, T cell subsets or T cell progenitors are gene modified by using viral and/or non-viral vectors.

Any of these steps may be multiplied, omitted or may occur in a different order.

In an embodiment of the invention, the modulatory agents are selected from agonistic antibodies and/or cytokines.

In an embodiment of the invention in said automated process, the gene-modified cells, preferentially T cells, T cell subsets or T cell progenitors are enriched by magnetic labelling of cells and magnetic separation before or after cultivation to obtain higher frequency of gene-modified cells, preferentially T cells, T cell subsets or T cell progenitors in the final cellular product.

As closed and sterile system for cell modification, the fully automated cell processing device CliniMACS Prodigy® and associated tubing sets (Miltenyi Biotec GmbH, Germany) may be used (WO2009/072003). This closed system meets the requirements of GMP-grade processing of almost any kind of cellular products and may allow reducing clean room requirements, improve technology transfer and harmonization of cell manufacturing processes. It has been developed to fully automate and standardize the manufacturing process of cellular therapeutic agents. The instrument can perform sample loading, cell washing, density-based cell separations including erythrocyte reduction and plasma harvesting, magnetic separation, cell activation, cell modification (transduction), cell culture, and final product formulation.

Thus enabling the flexible integration of process modules ("steps") in a closed, automated and safe GMP compliant workflow reproducing a complex desired biological process.

In one embodiment of the invention the SSEA4-CAR of the invention is used for treatment in a subject having a disease, disorder or condition associated with an abnormal expression of SSEA4.

In one embodiment of the invention the SSEA4-CAR of the invention is for use in treatment of cancer in a subject suffering from cancer, wherein at least a subpopulation of the cancerous cells of said cancer expresses SSEA4 such as human breast cancer, RCC and human ovarian cancer. Immune cells, e.g. T cells of a subject are isolated. The subject may suffer from said cancer or may be a healthy subject. These cells are genetically modified in vitro or in vivo? to express SSEA4-CAR. These engineered cells may be activated and expanded in vitro or in vivo?. In a cellular therapy these engineered cells are infused to a recipient in need thereof. These cells may be a pharmaceutical composition (said cell plus pharmaceutical acceptable carrier). The infused cells are able to kill (or at least stop growth of) cancerous cells expressing SSEA4 in the recipient. The recipient may be the same subject from which the cells was obtained (autologous cell therapy) or may be from another subject of the same species (allogeneic cell therapy).

In one embodiment of the invention the subject suffering from cancer may be treated with the pharmaceutical composition of the invention together with an immunomodulatory agent, such as but not limited to Rapamycin or agents blocking PD-1/PD-L1 or CTLA4 signaling.

In one embodiment of the invention, due to the fact that the cancerous cells expressing SSEA4 may be only a subpopulation of the cancerous cells of the subject the subject may be treated additionally with chemotherapy. Chemotherapeutic agents suited to treat cancers are well known in the art.

In another embodiment of the invention the subject suffering from said cancer may be treated by an additional targeted therapy, for example but not limited to antibody mediated Her2 targeting instead of the treatment with chemotherapy. Alternatively, the subject may also be treated by chemotherapy.

A method for assessing the prognosis associated to resistance to chemotherapy in an individual having a cancer is disclosed in EP14305477.3, the method comprising the steps of a) providing a sample to be tested, and b) detecting expression of SSEA4 in the test sample, wherein the expression of SSEA4 in the test sample is indicative of a poor prognosis. Therefore, in one embodiment of the invention the subject suffering from cancer is analyzed (a diagnosis is made) with respect to the kind of the cancer before treatment with the engineered cells of the invention. If the analysis of the cancer indicates that the cancer comprises at least a subpopulation of the cancerous cells which expresses SSEA4, then the treatment of the subject suffering from said cancer with SSEA4-CAR engineered cells is promising and advisable. But the subject suffering from cancer, wherein said cancer has no cancerous cells expressing SSEA4 may also be treated with the SSEA4-CAR engineered cells of the present invention as disclosed herein as a measure of precaution and prevention of the genesis of cancerous cells expressing SSEA4 during a treatment of the subject suffering from cancer e.g. a chemotherapeutical treatment.

In one embodiment of the invention the SSEA4-CAR expressing cells are applied to a subject suffering from cancer as cellular therapy as disclosed above but in combination with a second activating CAR, which is also expressed on the same engineered cells, recognizing an additional epitope to increase the specificity of the engineered cells expressing both CARs. This epitope can be membrane bound, part of the extracellular matrix, or a soluble component. In one embodiment of the invention the SSEA4-CAR expressing cells are applied to a subject suffering from cancer as cellular therapy as disclosed above but in combination with a second activating CAR, which is also expressed on the same engineered cells, recognizing an additional epitope on the cancerous cells expressing SSEA4 to increase the specificity of the engineered cells expressing both CARs. This epitope can be membrane bound, part of the extracellular matrix, or a soluble component.

In one embodiment of the invention the SSEA4-CAR expressing cells are applied to a subject suffering from cancer as cellular therapy as disclosed above but in combination with a second, inhibitory CAR, which is also expressed on the same engineered cells, recognizing an additional epitope to increase the specificity of the engineered cells expressing both CARs. This epitope can be membrane bound, part of the extracellular matrix, or a soluble component.

The immune cells, preferentially T cells engineered to express SSEA4-CAR may be administered either alone, or as a pharmaceutical composition in combination with diluents and/or with other components such as IL-2 or other cytokines or cell populations. Briefly, pharmaceutical compositions of the present invention may comprise a cell population of genetically modified cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Preferentially, the compositions of the present invention are formulated for intravenous administration. The administration of cell compositions to the subject may be carried out in any convenient manner known in the art.

Pharmaceutical compositions of the present invention may be administered in a manner appropriate to the disease to be treated. Appropriate dosages may be determined by clinical trials. But the quantity and frequency of administration will also be determined and influenced by such factors as the condition of the patient, and the type and severity of the patient's disease.

A pharmaceutical composition comprising the immune cells, preferentially T cells disclosed herein may be administered at a dosage of $10^4$ to $10^9$ cells/kg body weight, preferably $10^5$ to $10^6$ cells/kg body weight. The cell compositions may also be administered several times at these dosages. The compositions of cells may be injected directly into a tumor, lymph node, or site of infection.

The cells may be activated and expanded to therapeutic effective amounts using methods known in the art.

The cells of the invention may be used in combination with e.g. chemotherapy, radiation, immunosuppressive agents, antibodies or antibody therapies.

Definitions

Unless defined otherwise, technical and scientific terms used herein have the same meaning as commonly understood by one of ordinary skill in the art to which this invention belongs.

The term "resistance to chemotherapy" means that some of the cancerous cells (at least one cell) of the subject suffering from cancer are resisting the intended effect of a chemotherapeutic treatment.

The term "tumor" is known medically as a neoplasm. Not all tumors are cancerous; benign tumors do not invade neighboring tissues and do not spread throughout the body.

The term "cancer" is known medically as a malignant neoplasm. Cancer is a broad group of diseases involving unregulated cell growth. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

The terms "Chemotherapy" or "chemotherapeutic treatment" refer to the treatment of cancer (cancerous cells) with one or more cytotoxic anti-neoplastic drugs ("chemotherapeutic agents" or "chemotherapeutic drugs") as part of a standardized regimen. Chemotherapy may be given with a curative intent or it may aim to prolong life or to palliate symptoms. It is often used in conjunction with other cancer treatments, such as radiation therapy, surgery, and/or hyperthermia therapy. Traditional chemotherapeutic agents act by killing cells that divide rapidly, one of the main properties of most cancer cells. This means that chemotherapy also harms cells that divide rapidly under normal circumstances: cells in the bone marrow, digestive tract, and hair follicles. This results in the most common side-effects of chemotherapy: myelosuppression (decreased production of blood cells, hence also immunosuppression), mucositis (inflammation of the lining of the digestive tract), and alopecia (hair loss).

Some newer anticancer drugs (for example, various monoclonal antibodies or engineered cells like those of the present invention) are not indiscriminately cytotoxic, but rather target proteins that are abnormally expressed in cancer cells and that are essential for their growth. Such treatments are often referred to as "targeted therapy" (as distinct from classic chemotherapy) and are often used alongside traditional chemotherapeutic agents in antineoplastic treatment regimens.

Types of classic chemotherapeutic drugs to which the terms "chemotherapeutic drugs" and "chemotherapy" as used herein refer are:

Alkylating agents: Alkylating agents are the oldest group of chemotherapeutics in use today. They are so named because of their ability to alkylate many molecules, including proteins, RNA and DNA. This ability to bind covalently to DNA or RNA via their alkyl group is the primary cause for their anti-cancer effects. This leads to a form of programmed cell death called apoptosis. Alkylating agents will work at any point in the cell cycle and thus are known as cell cycle-independent drugs. For this reason the effect on the cell is dose dependent; the fraction of cells that die is directly proportional to the dose of drug. The subtypes of alkylating agents are the nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, Ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin. They impair cell function by forming covalent bonds with the amino, carboxyl, sulfhydryl, and phosphate groups in biologically important molecules. Non-classical alkylating agents include procarbazine and hexamethylmelamine. Mafosfamideis an oxazaphosphorine (cyclophosphamide-like) alkylating agent under investigation as a chemotherapeutic drug.

Anti-metabolites: The terms "anti-metabolites" and "DNA synthesis and transcription inhibitors" as used herein have an interchangeable meaning and define are a group of molecules that impede DNA and RNA synthesis. Many of them have a similar structure to the building blocks of DNA and RNA. Anti-metabolites resemble either nucleobases or nucleosides, but have altered chemical groups. These drugs exert their effect by either blocking the enzymes required for DNA synthesis or becoming incorporated into DNA or RNA. By inhibiting the enzymes involved in DNA synthesis, they prevent mitosis because the DNA cannot duplicate itself. Also, after misincorporation of the molecules into DNA, DNA damage can occur and programmed cell death (apoptosis) is induced. Unlike alkylating agents, anti-metabolites are cell cycle dependent. This means that they only work during a specific part of the cell cycle, in this case S-phase (the DNA synthesis phase). For this reason, at a certain dose, the effect plateaus and proportionally no more cell death occurs with increased doses. Subtypes of the anti-metabolites are the anti-folates, fluoropyrimidines, deoxynucleoside analogues and thiopurines. The anti-folates include methotrexate and pemetrexed. The fluoropyrimidines include fluorouracil and capecitabine. Fluorouracil is a nucleobase analogue that is metabolised in cells to form at least two active products; 5-fluourouridine monophosphate (FUMP) and 5-fluoro-2'-deoxyuridine 5'-phosphate (fdUMP). FUMP becomes incorporated into RNA and fdUMP inhibits the enzyme thymidylate synthase; both of which lead to cell death. Capecitabine is a prodrug of 5-fluorouracil that is broken down in cells to produce the active drug. The deoxynucleoside analogues include cytarabine, gemcitabine, decitabine, vidaza, fludarabine, nelarabine, cladribine, do farabine and pentostatin. The thiopurines include thioguanine and mercaptopurine Anti-microtubule agents: Anti-microtubule agents are plant-derived chemicals that block cell division by preventing microtubule function. Vinca alkaloids and taxanes are the two main groups of anti-microtubule agents. The vinca alkaloids prevent the formation of the microtubules, whereas the taxanes prevent the microtubule disassembly. By doing so, they prevent the cancer cells from completing mitosis. Following this, cell cycle arrest occurs, which induces programmed cell death (apoptosis). Vinca alkaloids are derived from the Madagascar periwinkle, Catharanthusroseus. Taxanes are natural and semi-synthetic drugs. The first drug of their class, paclitaxel, was originally extracted from the Pacific Yew tree, Taxusbrevifolia. Now this drug and another in this class, docetaxel, are produced semi-synthetically from a chemical found in the bark of another Yew tree; Taxusbaccata. These drugs promote microtubule stability, preventing their disassembly. Docetaxel exerts its effect during S-phase.

Topoisomerase inhibitors: Topoisomerase inhibitors are drugs that affect the activity of two enzymes; topoisomerase I and topoisomerase II. When the DNA double stranded helix is unwound, during DNA replication or translation for example, the adjacent unopened DNA winds tighter (supercoils), like opening the middle of a twisted rope. The stress caused by this effect is in part aided by the topoisomerase enzymes. They produce single or double strand breaks into DNA, reducing the tension in the DNA strand. This allows the normal unwinding of DNA to occur during replication or translation. Inhibition of topoisomerase I or II interferes with both of these processes. Two topoisomerase I inhibitors, irinotecan and topotecan, are semi-synthetically derived from camptothecin, which is obtained from the Chinese ornamental tree Camptothecaacuminata. Drugs that target topoisomerase II can be divided into two groups. The topoisomerase II poisons cause increased levels enzymes bound to DNA. This prevents DNA replication and translation, causes DNA strand breaks, and leads to programmed cell death (apoptosis). These agents include etoposide, doxorubicin, mitoxantrone and teniposide. The second group, catalytic inhibitors, are drugs that block the activity of topoisomerase II, and therefore prevent DNA synthesis and translation because the DNA cannot unwind properly. This group includes novobiocin, merbarone, and aclarubicin.

Cytotoxic antibiotics: The cytotoxic antibiotics are a varied group of drugs that have various mechanisms of action. The group includes the anthracyclines and other drugs including actinomycin, bleomycin, plicamycin and mitomycin. Doxorubicin and daunorubicin were the first two anthracyclines, and were obtained from the bacterium *Streptomyces peucetius*. Derivatives of these compounds include epirubicin and idarubicin. Other clinically used drugs in the anthracyline group are pirarubicin, aclarubicin and mitoxantrone. The mechanisms of anthracyclines include DNA intercalation (molecules insert between the two strands of DNA), generation of highly reactive free radicals that damage intercellular molecules and topoisomerase inhibition. Actinomycin is a complex molecule that intercalates DNA and prevents RNA synthesis. Bleomycin, a glycopeptide isolated from *Streptomyces verticillus*, also intercalates DNA, but produces free radicals that damage DNA. This occurs when bleomycin binds to a metal ion, becomes chemically reduced and reacts with oxygen. Mitomycin is a cytotoxic antibiotic with the ability to alkylate DNA.

Combination chemotherapy involves treating a patient with a number of different drugs simultaneously. The drugs differ in their mechanism and side effects. The biggest advantage is minimizing the chances of resistance developing to any one agent. Also, the drugs can often be used at lower doses, reducing toxicity. A prominent example is the combination of doxorubicin and cyclophosphamide (A/C).

"Resistance to chemotherapy" occurs when cancerous cells are not inhibited or killed by the treatment, at least at the concentration applied. In other words, the cancerous cells are resisting the effects of the chemotherapy. The term "sensitivity to chemotherapy" has a corresponding meaning.

The term "autologous" as used herein refers to any material derived from the same subject to who it is later re-introduced.

The term "allogeneic" as used herein refers to any material derived from a different subject of the same species as the subject to who the material is re-introduced.

The term "therapeutic effective amount" means an amount which provides a therapeutic benefit.

The term "isolated" means altered or removed from the natural state. For example an isolated population of cells means an enrichment of such cells and separation from other cells which are normally associated in their naturally occurring state with said isolated cells. An isolated population of cells means a population of substantially purified cells which are a homogenous population of cells.

The terms "specifically binds" or "specific for" with respect to an antigen-binding domain of an antibody, of a fragment thereof or of a CAR refer to an antigen-binding domain which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific.

The terms "engineered cell" and "genetically modified cell" as used herein can be used interchangeably. The terms mean containing and/or expressing a foreign gene or nucleic acid sequence which in turn modifies the genotype or phenotype of the cell or its progeny. Especially, the terms refer to the fact that cells, preferentially T cells can be manipulated by recombinant methods well known in the art to express stably or transiently peptides or proteins which are not expressed in these cells in the natural state. For example T cells are engineered to express an artificial construct such as a chimeric antigen receptor on their cell surface. For example, the CAR sequences may be delivered into cells using a retroviral or lentiviral vector.

The amino acid sequences of SSEA4 $V_H$, SSEA4 $V_L$, scFv $V_H$-linker-$V_L$, scFv $V_L$-linker-$V_H$, SSEA4-CAR $V_H$-linker-$V_L$ and SSEA4-CAR $V_L$-linker-$V_H$ are given in SEQ ID NO:1, SEQ ID NO:2, SEQ ID NO:3, SEQ ID NO:4, SEQ ID NO:5 and SEQ ID NO:6, respectively (in the one-letter code of amino acids). The amino acid sequences (proteins, polypeptides) as given in the SEQ ID NO1 to SEQ ID NO:6 refer to all constellations of the respective amino acid sequence which retains the intended function of the respective amino acid sequence as defined herein. In other words, the divergences to the SEQ ID No:1, SEQ ID NO:2, SEQ ID NO:3, SEQ ID NO:4, SEQ ID NO:5 and SEQ ID NO:6, respectively, should not affect their potential as binding specifically to the antigen SSEA4 and/or being a functional CAR. Therefore, the amino acid sequences of SEQ ID NO:1 to SEQ ID NO:6 can be the full length amino acid sequence of the SEQ ID NO:1 to SEQ ID NO:6, respectively. It can also be a variant thereof which have some amino acids deleted, added or replaced while still retaining the intended function as described herein. Therefore, included in this definition are variants of the amino acid sequences in SEQ ID NO: 1, SEQ ID NO:2, SEQ ID NO:3, SEQ ID NO:4, SEQ ID NO:5 and SEQ ID NO:6, respectively, such as amino acid sequences essentially similar to SEQ ID NO: 1, SEQ ID NO:2, SEQ ID NO:3, SEQ ID NO:4 and SEQ ID NO:5, respectively, having a sequence identity of at least 70%, or at least 75%, 80%, 85%, 90%, 95%, 97%, 98% or 99% at the amino acid sequence level. In the context of the present invention, "sequence identity" may be determined using pairwise alignments using alignments programs for amino acid sequences well known to the art.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4' T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, Th9, or $T_{FH}$, which secrete different cytokines to facilitate a different type of immune response. Signaling from the APC directs T cells into particular subtypes.

Cytotoxic T cells ($T_C$ cells, or CTLs) destroy virally infected cells and tumor cells, and are also implicated in transplant rejection. These cells are also known as CD8$^+$ T cells since they express the CD8 glycoprotein at their surface. These cells recognize their targets by binding to antigen associated with MHC class I molecules, which are present on the surface of all nucleated cells.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells ($T_{CM}$ cells) and two types of effector memory T cells ($T_{EM}$ cells and $T_{EMRA}$ cells). Memory cells may be either $CD4^+$ or $CD8^+$. Memory T cells typically express the cell surface protein CD45RO. Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of $CD4^+$ $T_{reg}$ cells have been described—Foxp3+$T_{reg}$ cells and Foxp3-$T_{reg}$ cells.

Natural killer T cells (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both $T_h$ and $T_c$ cells (i.e., cytokine production and release of cytolytic/cell killing molecules).

Immunotherapy is a medical term defined as the "treatment of disease by inducing, enhancing, or suppressing an immune response". Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based, preferentially T cell-based cytotoxic responses to attack cancer cells. T cells that have a natural or genetically engineered reactivity to a patient's cancer are generated in vitro and then transferred back into the cancer patient.

The term "treatment" as used herein means to reduce the frequency or severity of at least one sign or symptom of a disease.

The term "biomarker" or "marker" is widespread in the art and may broadly denote a biological molecule and/or a detectable portion thereof (e.g. a nucleic acid, a peptide or a lipid such as a glycolipid) whose qualitative and/or quantitative evaluation in an individual is predictive or informative (e.g., predictive, diagnostic and/or prognostic) with respect to one or more aspects of the individual's phenotype and/or genotype, such as, for example, with respect to the status of the individual. E.g. the biomarker is predictive or informative with respect to the outcome for chemotherapeutic treatment of a cancer in an individual. A biomarker is expressed ("expression of the biomarker") if the biomarker is detectable with methods known in the art. Therefore expression of biomarkers encompasses not only expression at nucleic acid level (DNA and/or RNA) and protein level but also expression (presence) of other biological structures on or in the cells such as glycolipids or the activity of a protein.

As used herein, the term "subject" refer to an animal. Preferentially, the subject is a mammal such as mouse, rat, cow, pig, goat, chicken dog, monkey or human. More preferentially, the individual is a human. The subject may be a subject suffering from a disease such as cancer (a patient), but the subject may be also a healthy subject.

The term "target" as used herein refers to an antigen or epitope associated with a cell that should be recognized specifically by an antigen binding domain, e.g. an antigen binding domain of an antibody or of a CAR. The antigen or epitope can be bound to the cell surface but also be secreted, part of the extracellular membrane, or shed from the cell.

The term "subpopulation of cancerous cells" as used herein refers to the fact that the cancerous cells of a cancer of a subject may be heterogeneous. As shown in EP14305477.3 in some cancers some cancerous cells express SSEA4 on their cell surface, others do not. Therefore the cancerous cells of a cancer of a subject expressing SSEA4 are a subpopulation (or a fraction) of cancerous cells within the cancer of said subject. The subpopulation may comprise at least one cell within all cancerous cells of the cancer of the subject. The subpopulation may comprise at least 1%, at least 5%, at least 10%, at least 15%, at least 20%, at least 25%, at least 30%, at least 35%, at least 40%, at least 45% or at least 50% of all cancerous cells of a subject suffering from said cancer.

The term "antibody" as used herein refers to polyclonal or monoclonal antibodies and fragments thereof, which can be generated by methods well known to the person skilled in the art. The antibody may be of any species, e.g. murine, rat, sheep, human. For therapeutic purposes, if non-human antigen binding fragments are to be used, these can be humanized by any method known in the art.

The antibodies may also be modified antibodies (e.g. oligomers, reduced, oxidized and labeled antibodies).

EXAMPLES

The following examples are intended for a more detailed explanation of the invention but without restricting the invention to these examples.

Example 1: Amino Acid Sequence of the SSEA4 Specific Antibody

The amino acid sequences of the variable portions of the immunoglobulin heavy chain and light chain of the used antibody specifically binding to SSEA4 were as given in SEQ ID NO:1 and SEQ ID NO:2, respectively.

These sequences or any sequences derived thereof with a specificity for SSEA4 can be used to generate a CAR recognizing SSEA4. The sequences given in SEQ ID NO:1 and SEQ ID NO:2 are only exemplary for sequences which are specific for the antigen SSEA4 (the sequences are given in one letter code for amino acids). Other sequences may be used for generating antigen binding domains of an antibody or of a CAR which are also specific for the antigen SSEA4.

Example 2: Structure of a CAR Recognizing SSEA4

The linkers used may comprise an epitope/tag allowing for the detection of the CAR as shown in FIG. 1. Examples for epitopes/tags are YOL, cMYC, or HIS. The anti-SSEA4 specific binding fragment is derived from an antibody specific for SSEA4. The hinge region may be derived e.g. from IgG domains, CD8α, or CD28 and may comprise an epitope/tag allowing for the detection of the CAR. The transmembrane domain may be derived e.g. from CD8α or CD28 followed by one to three signaling domains. These domains may be derived e.g. from CD28, 4-1BB, OX40, or CD3 zeta.

As specific sequences the following sequences were used.

For the antigen binding domain of the SSEA4-CAR scFv's were used having the amino acid sequences of either SEQ ID NO:3 or SEQ ID NO:4 (the sequences are given in one letter code of amino acids).

SEQ ID NO:5 and SEQ ID NO:6 (see also sequences in FIG. 2) represent full amino acid sequences (the sequences are given in one letter code of amino acids) of a CAR specific for the antigen SSEA4.

Example 3: Generation of Lentiviral Expression Vectors

The SSEA4-CARs were cloned into third generation SIN-lentiviral vector constructs under the control of the human PGK promoter. Transient transfection of HEK 293T cells with this expression plasmid and further plasmids encoding the structural proteins gag-pol, rev and VSV-G envelope protein resulted in the release of viral vector particles into the supernatant. The viral vector particles were subsequently enriched by low speed centrifugation and stored at −70° C.

Example 4: T Cell Separation and Genetic Modification with SSEA4-CAR

Primary T cells were isolated from donor apheresis or buffy coat samples using MicroBeads and MACS Technology® (Miltenyi Biotec GmbH, Germany) to reach purities of over 90% (CD3+ cells). Magnetically enriched cells were washed and resuspended in TexMACS medium supplemented with 200 IU/mL human recombinant IL-2 (Miltenyi Biotec GmbH, Germany). The T cells were then stimulated by addition of the GMP TransAct CD3/CD28 Reagent (Miltenyi Biotec GmbH, Germany).

After 24 hours, successful T cell stimulation was confirmed by staining the T cells with CD25 and CD69 antibodies and analysis by flow cytometry in a MACSQuant Analyzer (Miltenyi Biotec GmbH, Germany). The stimulated T cells were then transduced by adding lentiviral vectors encoding SSEA4-CAR at an MOI=0.5-2. After 4 days of static culture the cells were washed to remove excess viral vector and TransAct Reagent and were cultivated for a further 5-10 days. The efficiency of viral transduction was measured by staining the surface expression of SSEA4-CAR among live CD3+ cells using anti-human Fc fluorochrome and flow cytometry. The number of gene marked T cells ranged between 10 and 60%, depending on the MOI used.

Example 5: SSEA4-CAR Functionality

SSEA4 expressing target cells or cells not expressing SSEA4 were incubated for 5 hours with expanded T cells expressing SSEA4-CAR or, as a control, with non-transduced T cells at varied effector to target cell ratios. Specific target cell killing was analyzed by flow cytometry.

Alternatively, the effector cells were restimulated with cell lines which were SSEA4-positive or -negative. Cytokine production (IFN-γ, IL-2, TNF-α) as well as degranulation (CD107a) were analyzed by flow cytometry. Only T cells carrying the SSEA4-CAR were able to kill the target cells, showed increased cytokine production as well as degranulation marker upregulation.

```
                      Sequence listing

SEQ ID NO: 1
SSEA4 V_H
QVQLKESGPG LVAPSQSLSI TCTVSGFSLS SQGVYWVRQP
PGKGLEWLGA IWAGGSTNYN SALMSRLSIS KDNSKSQVFL
KMNSLQTDDT AMYYCARVDG YRGYNMDYWG QGTSVTVSS

SEQ ID NO: 2
SSEA4 V_L
ENVLTQSPAI MSASPGEKVT MTCSASSSVS YMHWYQQKSS
TSPKLWIYDT SKLASGVPGR FSGSGSGNSY SLTISSMEAE
DVATYYCFQG SGYPLTFGAG TKLELK

SEQ ID NO: 3
scFv V_H-linker-V_L
QVQLKESGPG LVAPSQSLSI TCTVSGFSLS SQGVYWVRQP
PGKGLEWLGA IWAGGSTNYN SALMSRLSIS KDNSKSQVFL
KMNSLQTDDT AMYYCARVDG YRGYNMDYWG QGTSVTVSSG
GGGSGGGGSG GGGSENVLTQ SPAIMSASPG EKVTMTCSAS
SSVSYMHWYQ QKSSTSPKLW IYDTSKLASG VPGRFSGSGS
GNSYSLTISS MEAEDVATYY CFQGSGYPLT FGAGTKLELK SEQ ID NO: 4
scFv V_L-linker-V_H
ENVLTQSPAI MSASPGEKVT MTCSASSSVS YMHWYQQKSS
TSPKLWIYDT SKLASGVPGR FSGSGSGNSY SLTISSMEAE
DVATYYCFQG SGYPLTFGAG TKLELKGGGG SGGGGSGGGG
SQVQLKESGP GLVAPSQSLS ITCTVSGFSL SSQGVYWVRQ
PPGKGLEWLG AIWAGGSTNY NSALMSRLSI SKDNSKSQVF
LKMNSLQTDD TAMYYCARVD GYRGYNMDYW GQGTSVTVSS SEQ ID NO: 5
Full CAR sequence: SSEA4-CAR V_H-linker-V_L
MDFQVQIFSF LLISASVIMS RQVQLKESGP GLVAPSQSLS
ITCTVSGFSL SSQGVYWVRQ PPGKGLEWLG AIWAGGSTNY
NSALMSRLSI SKDNSKSQVF LKMNSLQTDD TAMYYCARVD
GYRGYNMDYW GQGTSVTVSS GGGGSGGGGS GGGGSENVLT
QSPAIMSASP GEKVTMTCSA SSSVSYMHWY QQKSSTSPKL
WIYDTSKLAS GVPGRFSGSG SGNSYSLTIS SMEAEDVATY
YCFQGSGYPL TFGAGTKLEL KAAALPAEPK SPDKTHTCPP
CPAPPVAGPS VFLFPPKPKD TLMIARTPEV TCVVVDVSHE
DPEVKFNWYV DGVEVHNAKT KPREEQYNST YRVVSVLTVL
HQDWLNGKEY KCKVSNKALP APIEKTISKA KGQPREPQVY
TLPPSRDELT KNQVSLTCLV KGFYPSDIAV EWESNGQPEN
NYKTTPPVLD SDGSFFLYSK LTVDKSRWQQ GNVFSCSVMH
EALHNHYTQK SLSSLSPGKK IYIWAPLAGT CGVLLLSLVI
TLYCKRGRKK LLYIFKQPFM RPVQTTQEED GCSCRFPEEE
EGGCELLRVK FSRSADAPAY QQGQNQLYNE LNLGRREEYD
VLDKRRGRDP EMGGKPRRKN PQEGLYNELQ KDKMAEAYSE
IGMKGERRRG KGHDGLYQGL STATKDTYDA LHMQALPPR SEQ ID NO: 6
Full CAR sequence: SSEA4-CAR V_L-linker-V_H
MDFQVQIFSF LLISASVIMS RENVLTQSPA IMSASPGEKV
TMTCSASSSV SYMHWYQQKS STSPKLWIYD TSKLASGVPG
RFSGSGSGNS YSLTISSMEA EDVATYYCFQ GSGYPLTFGA
GTKLELKGGG GSGGGGSGGG GSQVQLKESG PGLVAPSQSL
SITCTVSGFS LSSQGVYWVR QPPGKGLEWL GAIWAGGSTN
YNSALMSRLS ISKDNSKSQV FLKMNSLQTD DTAMYYCARV
DGYRGYNMDY WGQGTSVTVS SAAALPAEPK SPDKTHTCPP
CPAPPVAGPS VFLFPPKPKD TLMIARTPEV TCVVVDVSHE
DPEVKFNWYV DGVEVHNAKT KPREEQYNST YRVVSVLTVL
HQDWLNGKEY KCKVSNKALP APIEKTISKA KGQPREPQVY
TLPPSRDELT KNQVSLTCLV KGFYPSDIAV EWESNGQPEN
NYKTTPPVLD SDGSFFLYSK LTVDKSRWQQ GNVFSCSVMH
EALHNHYTQK SLSSLSPGKK IYIWAPLAGT CGVLLLSLVI
TLYCKRGRKK LLYIFKQPFM RPVQTTQEED GCSCRFPEEE
EGGCELLRVK FSRSADAPAY QQGQNQLYNE LNLGRREEYD
VLDKRRGRDP EMGGKPRRKN PQEGLYNELQ KDKMAEAYSE
IGMKGERRRG KGHDGLYQGL STATKDTYDA LHMQALPPR
```

The invention claimed is:

1. A chimeric antigen receptor (CAR) comprising an antigen binding domain specific for sialyl-glycolipid stage-specific embryonic antigen 4 (SSEA4), wherein the antigen binding domain comprises the amino acid sequences of SEQ ID NO: 1 and SEQ ID NO: 2.

2. The CAR according to claim 1, wherein the CAR comprises a transmembrane domain and an intracellular signaling domain, wherein the transmembrane domain comprises an amino acid sequence of the transmembrane domain of at least one of CD8alpha and CD28; and wherein the intracellular signaling domain comprises an amino acid sequence of the intracellular signaling domain of one or more of CD28, CD137 and CD3zeta.

3. The CAR according to claim 1, wherein the CAR comprises the amino acid sequence of SEQ ID NO:5.

4. A method of treating cancer in a subject in need thereof, comprising administering to the subject an isolated population of engineered cells expressing the CAR according to claim 1, wherein at least a subpopulation of cancerous cells in the subject expresses SSEA4.

5. The method according to claim 4, wherein the subject is a human subject, and wherein said cancer is selected from the group consisting of human breast cancer, human renal cell carcinoma (RCC), and human ovarian cancer.

6. A population of engineered cells expressing the CAR according to claim 1.

7. The population of engineered cells according to claim 6, wherein said engineered cells are T cells or natural killer (NK) cells.

8. A pharmaceutical composition comprising an engineered cell expressing the CAR according to claim 1 and a pharmaceutical acceptable carrier.

9. The pharmaceutical composition according to claim 8, further comprising a chemotherapeutic agent.

10. An isolated nucleic acid comprising a nucleotide sequence encoding the CAR according to claim 1.

11. The method of claim 4, further comprising administering a chemotherapeutic agent to the subject.

12. The method of claim 4, wherein the subject is a human subject.

13. The CAR according to claim 1, wherein the CAR comprises the amino acid sequence of SEQ ID NO:6.

* * * * *

SEQUENCE LISTING

<160> NUMBER OF SEQ ID NOS: 6

<210> SEQ ID NO 1
<211> LENGTH: 119
<212> TYPE: PRT
<213> ORGANISM: Artificial Sequence
<220> FEATURE:
<223> OTHER INFORMATION: SSEA4 VH

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Gln
            20                  25                  30

Gly Val Tyr Trp Val Arg Gln Pro Pro Gly Lys Gly Leu Glu Trp Leu
        35                  40                  45

Gly Ala Ile Trp Ala Gly Gly Ser Thr Asn Tyr Asn Ser Ala Leu Met
50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Val Asp Gly Tyr Arg Gly Tyr Asn Met Asp Tyr Trp Gly Gln Gly
            100                 105                 110

Thr Ser Val Thr Val Ser Ser
        115

<210> SEQ ID NO 2
<211> LENGTH: 106
<212> TYPE: PRT
<213> ORGANISM: Artificial Sequence
<220> FEATURE:
<223> OTHER INFORMATION: SSEA4 VL

<400> SEQUENCE: 2

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Glu Leu Lys
            100                 105

<210> SEQ ID NO 3
<211> LENGTH: 240
<212> TYPE: PRT
<213> ORGANISM: Artificial Sequence
<220> FEATURE:
<223> OTHER INFORMATION: scFv VH-linker-VL

<400> SEQUENCE: 3

Gln Val Gln Leu Lys Glu Ser Gly Pro Gly Leu Val Ala Pro Ser Gln
1               5                   10                  15

```
Ser Leu Ser Ile Thr Cys Thr Val Ser Gly Phe Ser Leu Ser Ser Gln
            20                  25                  30

Gly Val Tyr Trp Val Arg Gln Pro Gly Lys Gly Leu Glu Trp Leu
        35                  40                  45

Gly Ala Ile Trp Ala Gly Gly Ser Thr Asn Tyr Asn Ser Ala Leu Met
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
            85                  90                  95

Arg Val Asp Gly Tyr Arg Gly Tyr Asn Met Asp Tyr Trp Gly Gln Gly
            100                 105                 110

Thr Ser Val Thr Val Ser Ser Gly Gly Gly Ser Gly Gly Gly Gly
            115                 120                 125

Ser Gly Gly Gly Gly Ser Glu Asn Val Leu Thr Gln Ser Pro Ala Ile
 130                 135                 140

Met Ser Ala Ser Pro Gly Glu Lys Val Thr Met Thr Cys Ser Ala Ser
145                 150                 155                 160

Ser Ser Val Ser Tyr Met His Trp Tyr Gln Gln Lys Ser Ser Thr Ser
            165                 170                 175

Pro Lys Leu Trp Ile Tyr Asp Thr Ser Lys Leu Ala Ser Gly Val Pro
            180                 185                 190

Gly Arg Phe Ser Gly Ser Gly Ser Gly Asn Ser Tyr Ser Leu Thr Ile
            195                 200                 205

Ser Ser Met Glu Ala Glu Asp Val Ala Thr Tyr Tyr Cys Phe Gln Gly
 210                 215                 220

Ser Gly Tyr Pro Leu Thr Phe Gly Ala Gly Thr Lys Leu Glu Leu Lys
225                 230                 235                 240

<210> SEQ ID NO 4
<211> LENGTH: 240
<212> TYPE: PRT
<213> ORGANISM: Artificial Sequence
<220> FEATURE:
<223> OTHER INFORMATION: scFv VL-linker-VH

<400> SEQUENCE: 4

Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
 50                  55                  60

Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Ser Gly Tyr Pro Leu Thr
            85                  90                  95

Phe Gly Ala Gly Thr Lys Leu Glu Leu Lys Gly Gly Gly Ser Gly
            100                 105                 110

Gly Gly Gly Ser Gly Gly Gly Gly Ser Gln Val Gln Leu Lys Glu Ser
        115                 120                 125

Gly Pro Gly Leu Val Ala Pro Ser Gln Ser Leu Ser Ile Thr Cys Thr
 130                 135                 140
```

```
Val Ser Gly Phe Ser Leu Ser Ser Gln Gly Val Tyr Trp Val Arg Gln
145                 150                 155                 160

Pro Pro Gly Lys Gly Leu Glu Trp Leu Gly Ala Ile Trp Ala Gly Gly
                165                 170                 175

Ser Thr Asn Tyr Asn Ser Ala Leu Met Ser Arg Leu Ser Ile Ser Lys
            180                 185                 190

Asp Asn Ser Lys Ser Gln Val Phe Leu Lys Met Asn Ser Leu Gln Thr
        195                 200                 205

Asp Asp Thr Ala Met Tyr Tyr Cys Ala Arg Val Asp Gly Tyr Arg Gly
    210                 215                 220

Tyr Asn Met Asp Tyr Trp Gly Gln Gly Thr Ser Val Thr Val Ser Ser
225                 230                 235                 240

<210> SEQ ID NO 5
<211> LENGTH: 679
<212> TYPE: PRT
<213> ORGANISM: Artificial Sequence
<220> FEATURE:
<223> OTHER INFORMATION: Full CAR sequence: SSEA4-CAR VH-linker-VL

<400> SEQUENCE: 5

Met Asp Phe Gln Val Gln Ile Phe Ser Phe Leu Leu Ile Ser Ala Ser
1               5                   10                  15

Val Ile Met Ser Arg Gln Val Gln Leu Lys Glu Ser Gly Pro Gly Leu
            20                  25                  30

Val Ala Pro Ser Gln Ser Leu Ser Ile Thr Cys Thr Val Ser Gly Phe
        35                  40                  45

Ser Leu Ser Ser Gln Gly Val Tyr Trp Val Arg Gln Pro Pro Gly Lys
    50                  55                  60

Gly Leu Glu Trp Leu Gly Ala Ile Trp Ala Gly Gly Ser Thr Asn Tyr
65                  70                  75                  80

Asn Ser Ala Leu Met Ser Arg Leu Ser Ile Ser Lys Asp Asn Ser Lys
                85                  90                  95

Ser Gln Val Phe Leu Lys Met Asn Ser Leu Gln Thr Asp Asp Thr Ala
            100                 105                 110

Met Tyr Tyr Cys Ala Arg Val Asp Gly Tyr Arg Gly Tyr Asn Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Gly Ser Glu Asn Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met His Trp Tyr Gln Gln
            180                 185                 190

Lys Ser Ser Thr Ser Pro Lys Leu Trp Ile Tyr Asp Thr Ser Lys Leu
        195                 200                 205

Ala Ser Gly Val Pro Gly Arg Phe Ser Gly Ser Gly Ser Gly Asn Ser
    210                 215                 220

Tyr Ser Leu Thr Ile Ser Ser Met Glu Ala Glu Asp Val Ala Thr Tyr
225                 230                 235                 240

Tyr Cys Phe Gln Gly Ser Gly Tyr Pro Leu Thr Phe Gly Ala Gly Thr
                245                 250                 255

Lys Leu Glu Leu Lys Ala Ala Ala Leu Pro Ala Glu Pro Lys Ser Pro
            260                 265                 270
```

```
Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ala Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Ser Leu Ser
                485                 490                 495

Pro Gly Lys Lys Ile Tyr Ile Trp Ala Pro Leu Ala Gly Thr Cys Gly
            500                 505                 510

Val Leu Leu Leu Ser Leu Val Ile Thr Leu Tyr Cys Lys Arg Gly Arg
        515                 520                 525

Lys Lys Leu Leu Tyr Ile Phe Lys Gln Pro Phe Met Arg Pro Val Gln
    530                 535                 540

Thr Thr Gln Glu Glu Asp Gly Cys Ser Cys Arg Phe Pro Glu Glu Glu
545                 550                 555                 560

Glu Gly Gly Cys Glu Leu Leu Arg Val Lys Phe Ser Arg Ser Ala Asp
                565                 570                 575

Ala Pro Ala Tyr Gln Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
        595                 600                 605

Asp Pro Glu Met Gly Gly Lys Pro Arg Arg Lys Asn Pro Gln Glu Gly
    610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
            660                 665                 670

Met Gln Ala Leu Pro Pro Arg
            675
```

```
<210> SEQ ID NO 6
<211> LENGTH: 679
<212> TYPE: PRT
<213> ORGANISM: Artificial Sequence
<220> FEATURE:
<223> OTHER INFORMATION: Full CAR sequence: SSEA4-CAR VL-linker- VH

<400> SEQUENCE: 6

Met Asp Phe Gln Val Gln Ile Phe Ser Phe Leu Leu Ile Ser Ala Ser
1               5                   10                  15

Val Ile Met Ser Arg Glu Asn Val Leu Thr Gln Ser Pro Ala Ile Met
            20                  25                  30

Ser Ala Ser Pro Gly Glu Lys Val Thr Met Thr Cys Ser Ala Ser Ser
        35                  40                  45

Ser Val Ser Tyr Met His Trp Tyr Gln Gln Lys Ser Ser Thr Ser Pro
    50                  55                  60

Lys Leu Trp Ile Tyr Asp Thr Ser Lys Leu Ala Ser Gly Val Pro Gly
65                  70                  75                  80

Arg Phe Ser Gly Ser Gly Ser Gly Asn Ser Tyr Ser Leu Thr Ile Ser
                85                  90                  95

Ser Met Glu Ala Glu Asp Val Ala Thr Tyr Tyr Cys Phe Gln Gly Ser
            100                 105                 110

Gly Tyr Pro Leu Thr Phe Gly Ala Gly Thr Lys Leu Glu Leu Lys Gly
        115                 120                 125

Gly Gly Gly Ser Gly Gly Gly Ser Gly Gly Gly Ser Gln Val
    130                 135                 140

Gln Leu Lys Glu Ser Gly Pro Gly Leu Val Ala Pro Ser Gln Ser Leu
145                 150                 155                 160

Ser Ile Thr Cys Thr Val Ser Gly Phe Ser Leu Ser Ser Gln Gly Val
                165                 170                 175

Tyr Trp Val Arg Gln Pro Pro Gly Lys Gly Leu Glu Trp Leu Gly Ala
            180                 185                 190

Ile Trp Ala Gly Gly Ser Thr Asn Tyr Asn Ser Ala Leu Met Ser Arg
        195                 200                 205

Leu Ser Ile Ser Lys Asp Asn Ser Lys Ser Gln Val Phe Leu Lys Met
    210                 215                 220

Asn Ser Leu Gln Thr Asp Asp Thr Ala Met Tyr Tyr Cys Ala Arg Val
225                 230                 235                 240

Asp Gly Tyr Arg Gly Tyr Asn Met Asp Tyr Trp Gly Gln Gly Thr Ser
                245                 250                 255

Val Thr Val Ser Ser Ala Ala Ala Leu Pro Ala Glu Pro Lys Ser Pro
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ala Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365
```

-continued

```
Glu Tyr Lys Cys Lys Val Ser Asn Lys Ala Leu Pro Ala Pro Ile Glu
        370             375             380
Lys Thr Ile Ser Lys Ala Lys Gly Gln Pro Arg Glu Pro Gln Val Tyr
385             390             395             400
Thr Leu Pro Pro Ser Arg Asp Glu Leu Thr Lys Asn Gln Val Ser Leu
            405             410             415
Thr Cys Leu Val Lys Gly Phe Tyr Pro Ser Asp Ile Ala Val Glu Trp
            420             425             430
Glu Ser Asn Gly Gln Pro Glu Asn Asn Tyr Lys Thr Thr Pro Pro Val
        435             440             445
Leu Asp Ser Asp Gly Ser Phe Phe Leu Tyr Ser Lys Leu Thr Val Asp
    450             455             460
Lys Ser Arg Trp Gln Gln Gly Asn Val Phe Ser Cys Ser Val Met His
465             470             475             480
Glu Ala Leu His Asn His Tyr Thr Gln Lys Ser Leu Ser Ser Leu Ser
                485             490             495
Pro Gly Lys Lys Ile Tyr Ile Trp Ala Pro Leu Ala Gly Thr Cys Gly
            500             505             510
Val Leu Leu Leu Ser Leu Val Ile Thr Leu Tyr Cys Lys Arg Gly Arg
    515             520             525
Lys Lys Leu Leu Tyr Ile Phe Lys Gln Pro Phe Met Arg Pro Val Gln
    530             535             540
Thr Thr Gln Glu Glu Asp Gly Cys Ser Cys Arg Phe Pro Glu Glu Glu
545             550             555             560
Glu Gly Gly Cys Glu Leu Leu Arg Val Lys Phe Ser Arg Ser Ala Asp
                565             570             575
Ala Pro Ala Tyr Gln Gln Gly Gln Asn Gln Leu Tyr Asn Glu Leu Asn
            580             585             590
Leu Gly Arg Arg Glu Glu Tyr Asp Val Leu Asp Lys Arg Arg Gly Arg
        595             600             605
Asp Pro Glu Met Gly Gly Lys Pro Arg Arg Lys Asn Pro Gln Glu Gly
        610             615             620
Leu Tyr Asn Glu Leu Gln Lys Asp Lys Met Ala Glu Ala Tyr Ser Glu
625             630             635             640
Ile Gly Met Lys Gly Glu Arg Arg Arg Gly Lys Gly His Asp Gly Leu
            645             650             655
Tyr Gln Gly Leu Ser Thr Ala Thr Lys Asp Thr Tyr Asp Ala Leu His
            660             665             670
Met Gln Ala Leu Pro Pro Arg
        675
```